US00PP24601P2

(12) United States Plant Patent
Nishita et al.

(10) Patent No.: US PP24,601 P2
(45) Date of Patent: Jul. 1, 2014

(54) ***PORTULACA* PLANT NAMED 'SAKPOR004'**

(50) Latin Name: *Portulaca oleracea*
Varietal Denomination: SAKPOR004

(71) Applicant: Sakata Seed Corporation, Yokohama (JP)

(72) Inventors: Koichi Nishita, Kakegawa (JP); Michiyoshi Fuyama, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 13/815,985

(22) Filed: Mar. 20, 2013

(51) Int. Cl.
*A01H 5/00* (2006.01)

(52) U.S. Cl.
USPC ..... Plt./471

(58) Field of Classification Search
USPC ..... Plt./471
See application file for complete search history.

(56) References Cited

U.S. PATENT DOCUMENTS

PP12,256 P2 * 12/2001 Matsukizono ..... Plt./471

OTHER PUBLICATIONS

Record Detail, retrieved from UPOV Search on Sep. 10, 2013, 1 page.*

* cited by examiner

*Primary Examiner* — June Hwu
*Assistant Examiner* — Keith Robinson
(74) *Attorney, Agent, or Firm* — James M. Weatherly; Cochran Freund & Young LLC

(57) ABSTRACT

A *Portulaca* plant particularly distinguished by having a gold flower color, flower blooming period from spring to fall and vigorous, semi-mounding and upright plant growth habit, is disclosed.

1 Drawing Sheet

Genus and species: *Portulaca oleracea.*
Variety denomination: 'SAKPOR004'.

BACKGROUND OF THE NEW PLANT

The present invention comprises a new and distinct variety of *Portulaca* plant, botanically known as *Portulaca oleracea*, and referred to by the variety name 'SAKPOR004'. *Portulaca* line 'SAKPOR004' originated from a hybridization in Kakegawa, Japan in 2006 between the female *Portulaca* line 'Mo04-24B-V2', an unpatented proprietary *Portulaca* breeding line having a gold flower color and bushy growth habit and the male *Portulaca* line 'Ma01-3A-1B1', an unpatented proprietary *Portulaca* breeding line with a gold flower color and bushy growth habit.

In August 2006, the female parent line 'Mo04-24B-V2' and male parent line 'Ma01-3A-1B1' were crossed and $F_1$ seeds were obtained. In May 2007, the $F_1$ seed was sown in the greenhouse, cultivated and plant lines were produced with gold colored flowers with a bushy plant habit. The plants were evaluated and plant line 'K2008-105' was selected for its gold flower color, flower blooming period from spring to fall and vigorous plant growth habit. In May 2008, line 'K2008-105' was vegetatively propagated, cultivated and evaluated. In August 2008, line 'K2008-105' was confirmed to be fixed and stable. Line 'K2008-105' was propagated and cultivated again in May 2009, May 2010 and May 2011 to reconfirm the stability of the line. Line 'K2008-105' was subsequently named 'SAKPOR004' and its unique characteristics were found to reproduce true to type in successive generations of asexual propagation via vegetative cuttings.

SUMMARY

The following are the most outstanding and distinguishing characteristics of this new variety when grown under normal horticultural practices in Salinas, Calif.

1. Gold flower color;
2. Flower blooming period from spring to fall; and
3. Vigorous, semi-mounding and upright plant growth habit.

DESCRIPTION OF THE PHOTOGRAPHS

This *Portulaca* plant is illustrated by the accompanying photographs which show the plant's overall plant habit including form, foliage, and flowers. The photographs are of a twelve-month-old plant grown in Salinas, Calif. under greenhouse conditions in the fall of 2012. The colors shown are as true as can be reasonably obtained by conventional photographic procedures.

DESCRIPTION OF THE NEW VARIETY

Figure 1:
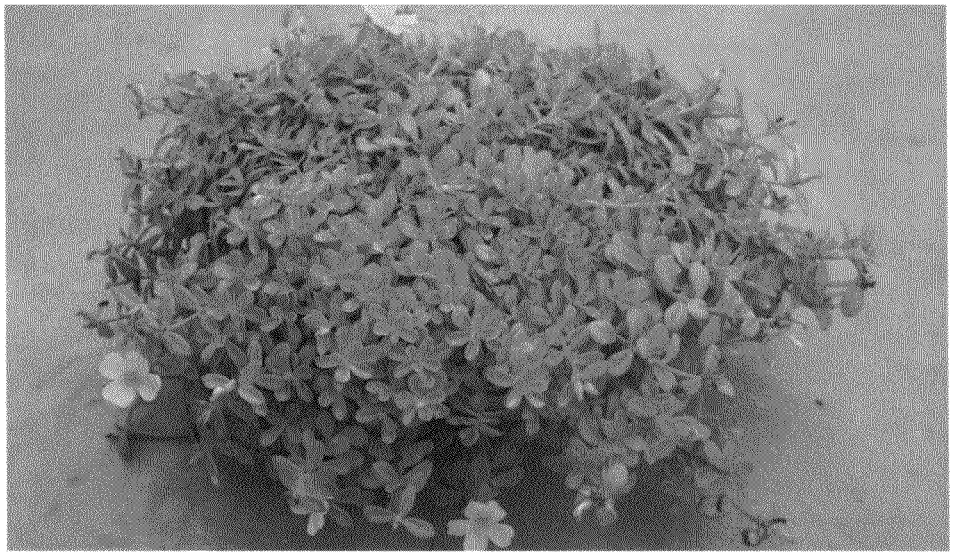
FIG. 1 shows the overall plant habit of the plant grown in a pot.
Figure 2:
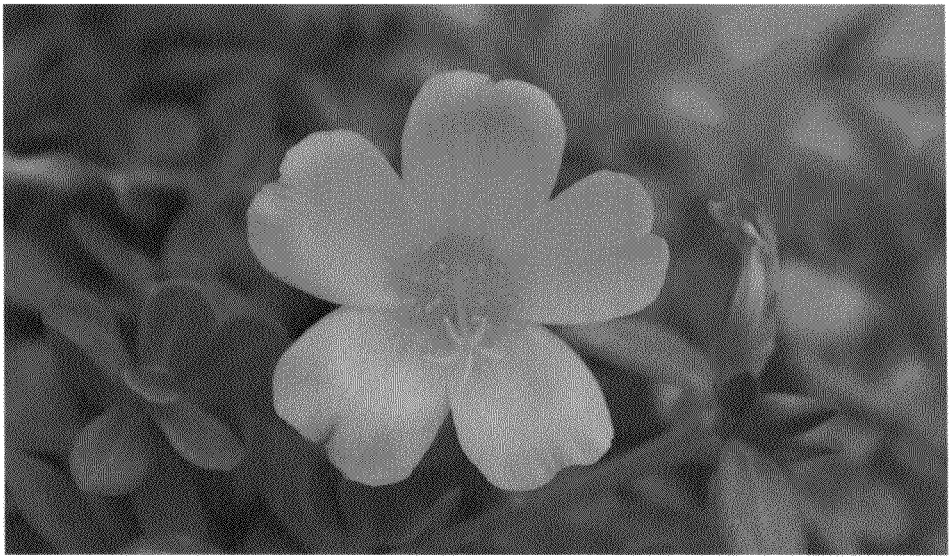
FIG. 2 shows a close-up of the mature inflorescence of the plant.

The following detailed descriptions set forth the distinctive characteristics of 'SAKPOR004'. The data which define these characteristics were collected from asexual reproductions carried out in Salinas, Calif. Data was collected on twelve-month-old plants grown under greenhouse conditions in Salinas, Calif. in the fall of 2012. Color references are to The R.H.S. Colour Chart of The Royal Horticultural Society of London (R.H.S.), 4th edition (2001).

Classification:

*Family*.—Portulacaceae.

*Botanical*.—*Portulaca oleracea*.

*Common*.—Purslane.

*Designation*.—'SAKPOR004'.

Parentage:

*Female parent*.—Proprietary *Portulaca* line 'Mo04-24B-V2' (unpatented).

*Male parent*.—Proprietary *Portulaca* line Ma01-3A-1B1' (unpatented).

Growth:

*Time to produce a rooted cutting*.—About 2 weeks.

*Environmental conditions for plant growth*.—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW™ (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Habit and form*.—Vigorous, semi-mounding and upright.

*Life cycle*.—Annual.

*Height* (*from soil line to top of foliage*).—Approximately 10.0 cm.

*Spread*.—Approximately 40.0 cm.

*Flowering requirements*.—Blooms repeatedly from spring to fall.

Stems:

*General description*.—Round, slightly rough with lateral ridges.

*Stem length*.—15.0 cm.

*Diameter*.—0.3 cm.

*Internode length* (*average*).—1.0 cm.

*Color*.—RHS 182B (Greyed-Red).

*Pubescence*.—Absent.

*Anthocyanin color*.—RHS 182B (Greyed-Red).

*Branching*.—Abundant.

Leaves:

*Arrangement*.—Alternate.

*Shape*.—Oblanceolate with cuspidate tip in mature leaves and acute tips in younger leaves near the apex of the stem.

*Apex*.—Acute.

*Base*.—Rounded.

*Margin*.—Entire.

*Surface appearance* (*both surfaces*).—Dull, soft.

*Surface pubescence* (*both surfaces*).—Absent.

*Length*.—2.0 cm.

*Width*.—1.2 cm.

*Texture*.—Smooth.

*Thickness*.—0.1 cm.

*Color*.—Upper surface: Mature leaves: Closest to RHS 146C (Yellow-Green) with RHS 59B (Red-Purple) at edge. Young leaves: RHS 146C (Yellow-Green). Lower surface: Mature leaves: Closest to RHS 146C (Yellow-Green) with RHS 59B (Red-Purple) at edge. Young leaves: RHS 146C (Yellow-Green).

*Venation*.—Absent.

*Petiole*.—Absent.

*Fragrance*.—Absent.

Inflorescence:

*Inflorescence type*.—Solitary, sessile.

*Flowering habit*.—Determinate.

*Time to bloom from propagation*.—6 to 8 weeks.

*Lastingness of individual blooms on the plant*.—1 day.

*Fragrance*.—Absent.

Flower bud:

*Surface texture*.—Shiny, pubescent.

*Length*.—1.0 cm.

*Diameter*.—0.5 cm.

*Shape*.—Lanceolate.

*Color*.—RHS 146C (Yellow-Green) with RHS 59B (Red-Purple).

Corolla:

*Shape*.—Five distinct petals, free with an indent at tip of petal.

*Flower diameter*.—3.5 cm.

*Flower depth*.—1.5 cm.

*Petals*.—Shape: Heart-shaped with a square base. Apex: Retuse. Base: Square. Margin: Double lobed, slightly sinuate. Surface texture (both surfaces): Glabrous. Length: 1.5 cm. Width: 1.0 cm. Color: Upper surface: RHS 12A (Yellow). Lower surface: RHS 12B (Yellow).

Calyx:

*Arrangement*.—Composed of two sepals, free.

*Sepals*.—Shape: Elliptic. Apex: Cuspidate. Margin: Entire, slightly sinuate. Color (both surfaces): Closest to RHS 146D (Yellow-Green). Texture (both surfaces): Double lobed, slightly sinuate, smooth. Length: 0.6 cm. Diameter: 0.5 cm.

Reproductive organs: Androecium.

*Stamen number*.—Many.

*Stamen color*.—RHS 7A (Yellow).

*Stamen form*.—Free.

*Filament color*.—RHS 7A (Yellow).

*Stamen length*.—0.6 cm.

*Pollen color*.—RHS 17A (Yellow-Orange).

*Pollen amount*.—Abundant.

*Ovary diameter*.—0.3 cm.

*Ovary color*.—RHS 143C (Green).

*Placental arrangement*.—Central.

*Pistil number*.—1 (per inflorescence).

*Pistil length*.—0.5 cm.

*Stigma color*.—RHS 2A (Yellow).

*Stigma length*.—0.2 cm.

*Style length*.—0.3 cm.

*Style color*.—RHS 7A (Yellow).

*Seed production*.—Absent.

Disease and insect resistance: None observed.

COMPARISON WITH PARENTAL LINES AND KNOWN VARIETY

'SAKPOR004' is a new and unique variety of *Portulaca* owing to its gold flower color, flower blooming period from spring to fall and vigorous, semi-mounding and upright plant growth habit. 'SAKPOR004' is distinguished from its parents mainly by plant growth habit as shown in Table 1 below:

TABLE 1

Comparison with Parental Lines

| Characteristic | 'SAKPOR004' | Female Parent 'Mo04-24B-V2' | Male Parent 'Mo01-3A-1B1 |
|---|---|---|---|
| Flower color | Gold | Gold | Gold |
| Plant growth habit | Vigorous, semi-mounding, upright | Bushy | Bushy |

'SAKPOR004' is a new and unique variety of *Portulaca* owing to its gold flower color, flower blooming period from spring to fall and vigorous, semi-mounding and upright plant growth habit. 'SAKPOR004' is most similar to the commercial *Portulaca* variety Pazzaz 'Jumbo Yellow' or 'DPAZ16' (U.S. Plant Pat. No. 23,244); however there are differences as described in Table 2 below.

TABLE 2

Comparison with Similar Variety

| Characteristic | 'SAKPOR004' | PAZZAZ ™ 'Jumbo Yellow' |
|---|---|---|
| Flower petal color, upper surface | RHS 12A (Yellow) | RHS 9A (Yellow) |
| Flower petal color, lower surface | RHS 12B (Yellow) | RHS 6B (Yellow) |
| Flower Size (Diameter) | 3.5 cm | 4.5 cm |
| Plant growth habit | Vigorous, semi-mounding and upright | Semi-trailing, medium |

We claim:

1. A new and distinct variety of *Portulaca* plant as shown and described herein.

* * * * *